United States Patent [19]

Hauck et al.

[11] Patent Number: 5,284,136
[45] Date of Patent: * Feb. 8, 1994

[54] DUAL INDIFFERENT ELECTRODE PACEMAKER

[75] Inventors: John A. Hauck, Shoreview; Brian D. Pederson, St. Paul, both of Minn.

[73] Assignee: Cardiac Pacemakers, Inc., St. Paul, Minn.

[*] Notice: The portion of the term of this patent subsequent to Aug. 6, 2008 has been disclaimed.

[21] Appl. No.: 698,789

[22] Filed: May 13, 1991

Related U.S. Application Data

[63] Continuation-in-part of Ser. No. 503,991, Apr. 4, 1990, Pat. No. 5,036,849.

[51] Int. Cl.⁵ ............................................. A61N 1/362
[52] U.S. Cl. .................................................... 607/24
[58] Field of Search ................................. 128/419 PG

[56] References Cited

U.S. PATENT DOCUMENTS

| | | | |
|---|---|---|---|
| 3,593,718 | 7/1971 | Krasner | 128/419 PG |
| 4,567,892 | 2/1986 | Plicchi | 128/419 PG |
| 4,576,183 | 3/1986 | Plicchi | 128/419 PG |
| 4,596,251 | 6/1986 | Plicchi | 128/419 PG |
| 4,686,987 | 8/1987 | Salo | 128/419 PG |
| 4,702,253 | 10/1987 | Nappholz | 128/419 PG |
| 4,722,342 | 2/1988 | Amundson | 128/419 PG |
| 4,776,338 | 10/1988 | Leckholm | 128/419 PG |
| 4,790,318 | 12/1988 | Elmquist | 128/419 PG |
| 4,884,576 | 12/1989 | Alt | 128/419 PG |
| 4,901,725 | 2/1990 | Nappholz | 128/419 PG |
| 4,919,136 | 4/1990 | Alt | 128/419 PG |

Primary Examiner—Kyle L. Howell
Assistant Examiner—Scott M. Getzow
Attorney, Agent, or Firm—Haugen and Nikolai

[57] ABSTRACT

An endocardial lead having first and second spaced apart electrodes resides in a patient's heart. The first electrode is a sensing electrode and the second electrode is a carrier signal driving electrode. The lead has a conductor coupling a source of alternating current carrier signals of a predetermined frequency to the second electrode. A third electrode is in electrical contact with body tissues. A cardiac pacer apparatus includes a pacer can which functions as a fourth electrode and has a plastic top wherein the third electrode is located. Said third electrode acts in cooperation with the first electrode to form a pair of sensing electrodes. The sensing electrode pair is further coupled to a sense amplifier for receiving an amplifying modulated electrical signals developed across the sensing electrode pair. A demodulator and filters circuit for demodulating the modulated carrier signal and recovering the modulating signal therefrom is connected to the output of the sense amplifier. The modulating signal is proportional to instantaneous stroke volume of the patient's heart and the demodulator and filters circuit develops a control signal therefrom called a stroke volume signal. The control signal is applied to the pulse generator so as to control the rate of stimulating pulses.

9 Claims, 3 Drawing Sheets

DUAL INDIFFERENT ELECTRODE PACEMAKER

CROSS-REFERENCE TO RELATED APPLICATION

This is a continuation-in-part of application Ser. No. 7/503,991, filed Apr. 4, 1990, now U.S. Pat. No. 5,036,849.

FIELD OF THE INVENTION

This invention relates broadly to the art of implantable medical devices and, more particularly, to apparatus having dual indifferent electrodes which allow the implementation of an implanted tetrapolar impedance system that requires only a bipolar pacing lead. Such an apparatus finds use in a tetrapolar impedance system that provides a stroke volume signal and a ventilatory signal using any bipolar pacing lead. In a further aspect, the dual indifferent electrode of the invention also facilitates a tripolar impedance technique using only a unipolar endocardial lead.

BACKGROUND OF THE INVENTION

The stroke volume of the heart has been recognized as providing a useful signal to control the timing circuit of a demand-type cardiac pacer. In such a system, the pacer pulse generator will output stimulating pulses in accordance with the physiologic demand indicated by stroke volume changes in the patient's heart. In U.S. Pat. No. 4,686,987 to Salo, et al., entitled "Biomedical Method and Apparatus for Controlling the Administration of Therapy to a Patient in Response to Changes in Physiologic Demand", a biomedical apparatus capable of sensing changes in the heart's ventricular volume or stroke volume is disclosed. The apparatus changes the operating performance of the device as a function of stroke volume. The teachings of U.S. Pat. No. 4,686,987 are hereby incorporated by reference. Salo, et al. teaches that a relatively low frequency signal (under 5 KHz) is applied between spaced electrodes disposed in the heart. The beating action of the heart serves to modulate the signal due to changes in impedance being sensed between these or other electrodes within the heart. The modulated carrier signal is processed to remove R-Wave and other electrical artifacts and then demodulated to remove the carrier frequency component, leaving an envelope signal which is proportional to instantaneous ventricular volume. This envelope signal then contains stroke volume and ventricular volume information which can be used by the biomedical apparatus to vary its operating parameters. For example, a current proportional to changes in the stroke volume may be injected into the timing circuit of a demand-type cardiac pacer pulse generator whereby the interpulse interval of the pulse generator is varied as a function of stroke volume.

A copending application assigned to the assignee of this application having U.S. patent application Ser. No. 07/664,461, filed Mar. 1, 1991, and entitled "Variation In Cardiac Chamber Volume or Pressure as a Controlling Parameter", is also incorporated herein by reference. The aforereferenced application recognizes that the ventilatory signal also appears as a component of the impedance signal. Because the intrathoracic pressure is directly related to ventilation (i.e. pressure drops during inspiration and increases during expiration), the amplitude of the variation in intrathoracic pressure during a ventilatory cycle is directly related to the depth of ventilation (i.e. respiration). U.S. patent application Ser. No. 07/664,461 provides an impedance system for measurement of right ventricular (or atrial) volume or a pressure transducer for measurement of right ventricular (or atrial) pressure, a signal processing means to extract one of the volume or pressure parameters on a beat-by-beat basis to thereby yield a signal varying at the ventilatory rate and with a peak-to-peak amplitude proportional to ventilatory depth.

Referring again to the Salo, et al. patent, for example, a cardiac lead having two sensing electrodes and a stimulating electrode is used. Often, in the case of a cardiac pacer replacement, a bipolar lead having only two electrodes has previously been implanted in the heart. In such cases, since it is desirable to use the already implanted lead with a new pacemaker system in the case of, for example, replacing a worn-out pacemaker, the three electrode lead as used by Salo, et al. is often not available. In such cases, only three electrodes are typically available, namely, the pulse generator case or can, a lead ring on the endocardial lead and a tip electrode on the endocardial lead. Prior approaches to implementing an intracardiac impedance system with only three electrodes available have used at least one electrode as a simultaneous drive and sense electrode, since two drive and two sense points are required. Such approaches have several disadvantages.

One disadvantage of prior art techniques results from a high current density region being sensed at the "common" electrode (i.e., the electrode being used as both a drive and sense electrode) making it very sensitive to local effects such as, for example, mechanical motion. Another disadvantage of prior art systems results from the interface impedance at the common electrode which presents a large DC offset when sensed, yielding a lower modulation index relative to that experienced with tetrapolar impedance. Yet another drawback of prior art systems is that if the common electrode is on the pacemaker lead, either the ring or the tip, system performance will vary as a function of electrode material, effective surface area, geometry and various other electrode characteristics.

The method of the present invention uses tetrapolar impedance techniques and overcomes the above described disadvantages of prior art devices. Since the present invention effectively implements a tetrapolar impedance system that provides a stroke volume signal using any bipolar pacing lead, the quality of the sensed stroke volume signal equals that of a tetrapolar system using a pulse generator can and a tripolar pacing lead. In a further aspect, the signal sensed with the present invention contains a lower frequency component due to ventilation. This component may be extracted as it is related to tidal volume and may be used as another rate controlling parameter.

The present invention also affords an advantage even when used on a unipolar pacing lead. Although a tetrapolar method is not possible for intra-cardiac use in such a case, the dual indifferent method provided by the invention allows a tripolar technique. This has the advantages of reduced motion artifact at the pacer can, as well as a lower DC offset.

SUMMARY OF THE INVENTION

This invention provides apparatus for use in a variable rate pacer apparatus responsive to the metabolic needs of the patient. In carrying out the instant invention and in accordance with a first embodiment, an endocardial lead having first and second spaced apart electrodes resides in a patient's heart. The first electrode is a sensing electrode and the second electrode is a carrier signal driving electrode. The lead has conductors coupling a source of alternating current carrier signals of a predetermined frequency to the second electrode. A third electrode is in electrical contact with body tissues. The pacer can functions as a fourth electrode and has a plastic top wherein the third electrode is located. Either the pacer can or the third electrode may be coupled to the carrier signals and acts in cooperation with the second electrode to form a pair of driving electrodes. The first electrode and either the third electrode or the can may comprise a sensing electrode pair. The sensing electrode pair is coupled to a sense amplifier means for receiving and amplifying modulated electrical signals developed across the sensing electrode pair. A demodulator and filters circuit means for demodulating the modulated carrier signal and recovering the modulating signal therefrom is connected to the output of the sense amplifier means. The modulating signal contains components proportional to instantaneous stroke volume of the patient's heart and the patient's ventilatory tidal volume, and the demodulator and filters circuit develops control signals therefrom called stroke volume and ventilation signals respectively. The control signals may be applied individually or in combination to the pulse generator so as to control the rate of stimulating pulses in accordance with a predetermined rate control algorithm.

It is one object of the invention to provide an implanted tetrapolar impedance system that requires only a bipolar endocardial lead.

It is another object of the invention to provide an implanted tripolar impedance system that requires only a unipolar endocardial lead.

It is yet another object of the invention to provide a button electrode electrically isolated from a pacemaker can and having a surface area on the same order as that for a lead ring electrode of an endocardial lead.

It is yet another object of the invention to provide an effective implementation of a tetrapolar impedance system that provides a stroke volume signal using any bipolar pacing lead wherein the quality and pulsatile morphology of the signal equals that of a tetrapolar system using a pulse generator can and a tripolar pacing lead as electrodes.

It is yet another object of the invention to provide an effective implementation of a tetrapolar impedance system that provides a ventilation signal free from can motion artifact using any bipolar pacing lead.

Other objects, features and advantages of the invention will become apparent to those skilled in the art through the description, claims and drawings herein.

DESCRIPTION OF THE PREFERRED EMBODIMENT

Figure 1:
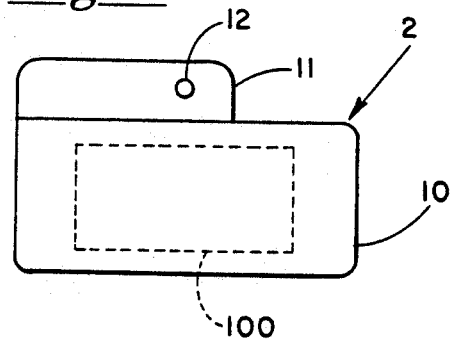
FIG. 1 schematically shows a pacer apparatus having a dual indifferent electrode apparatus.

Referring to FIG. 1 there is diagrammatically shown a side view of a pacemaker apparatus 2 comprised of a conductive metal can 10 and an insulating top or header 11. Mounted in the top 11 and isolated from the metal can 10 is a button electrode 12. Contained within the can 10 is electronic circuit 100 which is explained in more detail below and which comprises the dual indifferent electrode circuitry.

Figure 2:
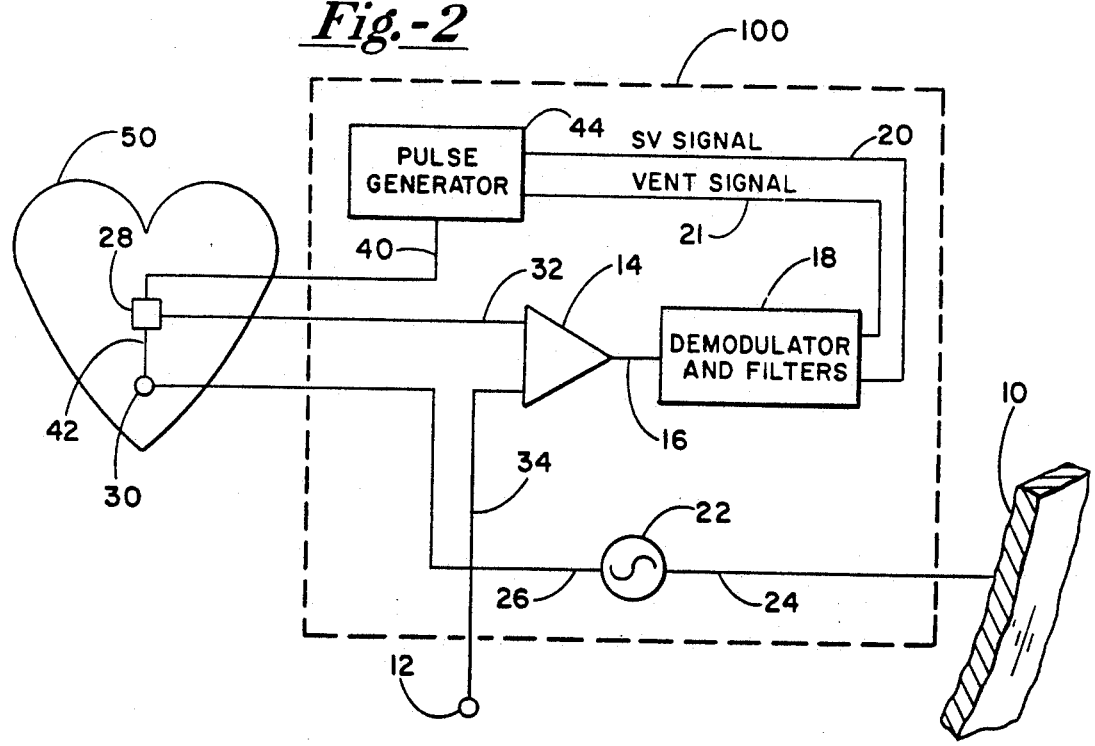
FIG. 2 schematically shows one embodiment of a dual indifferent electrical apparatus for use in an implantable heart pacemaker in accordance with the invention.

Now, referring to FIG. 2, the circuit 100 is shown in more detail. The can 10 is connected by lead 24 to an oscillator 22 which serves as a carrier current source. An endocardial lead 40 is connected to a pulse generator 44 which is contained within the pacemaker 2. The lead 40 includes electrodes 28 and 30 located within one of the chambers of the heart 50. Electrode 30 may be, for example, a stimulating tip electrode on a catheter type lead while electrode 28 may be, for example, a ring electrode. Insulator lead body 42 mechanically supports electrodes 28 and 30. The oscillator 22 is arranged to produce an alternating current carrier signal at a frequency which is quite high compared to the heart rate. Typically the carrier signal is in the range of from about 500 to 20000 Hz. In the arrangement of FIG. 2, the carrier signal is driven by electrode 30 through body tissues to the can 10. Button electrode 12 has a surface area typically on the same order of magnitude as the surface area of ring electrode 28 and is advantageously disposed on the plastic top 11 of the implantable pacemaker 2. In the embodiment of FIG. 2, the button electrode 12 is connected via lead 34 to a first input of a differential amplifier 14. Ring electrode 28 is also connected via lead 32 to a second input of differential amplifier 14. The output of differential amplifier 14 is carried via conductor 16 into demodulator and filters circuit 18. The demodulator and filters circuit 18 is connected by line 20 to the pulse generator. The demodulator and filters circuit 18 may include signal processing circuits as are shown in U.S. Pat. No. 4,686,987, as well as filtering means to separate the higher frequency stroke volume signal from the lower frequency ventilation signal as shown in U.S. patent application Ser. No. 07/664,461.

In operation, the pulse generator 44 provides stimulating pulses to stimulating electrodes in a well known manner to pace the heart. Electrodes 28 and 12 sense electrical impedance variations in the thoracic cavity which may be due to the pumping action of the heart or other physiological signals of interest. The signals are fed into the differential sense amplifier 14 which provides a differential signal to the demodulator and filters circuit 18. The demodulator and filters circuit includes means for demodulating the modulated carrier signal and recovering the modulating envelope signal therefrom. The modulating signal is found to contain frequency components proportional to the instantaneous stroke volume of the patient's heart and to the instantaneous tidal volume of the patient's ventilation. The demodulator and filters circuit 18 then provides control signals, SV SIGNAL 20 and VENT SIGNAL 21 to the pulse generator. The pulse generator responds to the control signal by determining a rate at which the heart stimulating pulses will be generated.

Figure 3:
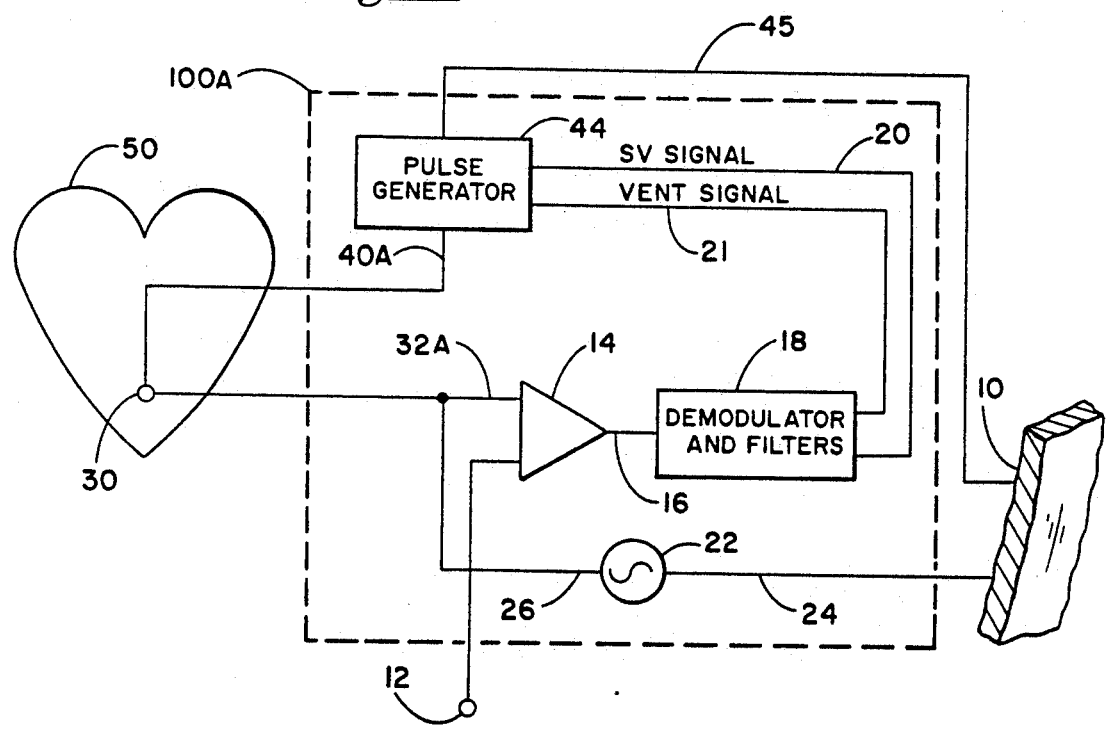
FIG. 3 schematically shows an alternate embodiment of a dual indifferent electrode apparatus as employed with a unipolar endocardial lead.

Now referring to FIG. 3, an alternate embodiment of the invention is shown as employed with a unipolar endocardial lead. In this embodiment, it will be understood that circuit 100A is similar to circuit 100 except that it is modified to accommodate unipolar pacing and sensing techniques. In this embodiment, the can 10 is connected by lead 24 to the oscillator 22 which serves as a carrier current source. The endocardial lead 40A is connected to a pulse generator 44 which is contained within the pacemaker 2. Lead 45 connects the pulse generator to the can 10 which, in this case, serves as a stimulating electrode. The lead 40A includes electrode 30 located within one of the chambers of the heart 50. Electrode 30 may be, for example, a tip electrode on a catheter type lead. The oscillator 22 is arranged to produce an alternating current carrier signal at a frequency which is quite high compared to the heart rate. Typically the carrier signal is in the range of from about 500 to 20000 Hz. The carrier signal is driven by electrode 30 through body tissues to the can 10. Button electrode 12 has a surface area typically on the same order of magnitude as the surface area of electrode 30 and is advantageously disposed on the plastic top 11 of the implantable pacemaker 2. The button electrode 12 is connected via lead 34 to a first input of a differential amplifier 14. Tip electrode 30 is also connected via lead 32A to a second input of differential amplifier 14. The output of differential amplifier 14 is carried via conductor 16 into demodulator and filters circuit 18. The demodulator and filters circuit 18 are connected by lines 20 and 21 to the pulse generator. The circuit 18 is configured as described above with reference to FIG. 2.

In operation, the pulse generator 44 provides stimulating pulses to stimulating electrodes in a well known manner to pace the heart. Electrodes 30 and 12 sense stroke volume impedance signals or other physiological signals of interest. The signals are fed into the differential amplifier 14 which provides a differential signal to the circuit 18. The demodulator and filters circuit operates as described above with reference to FIG. 2.

ALTERNATIVE EMBODIMENTS

Figure 4:
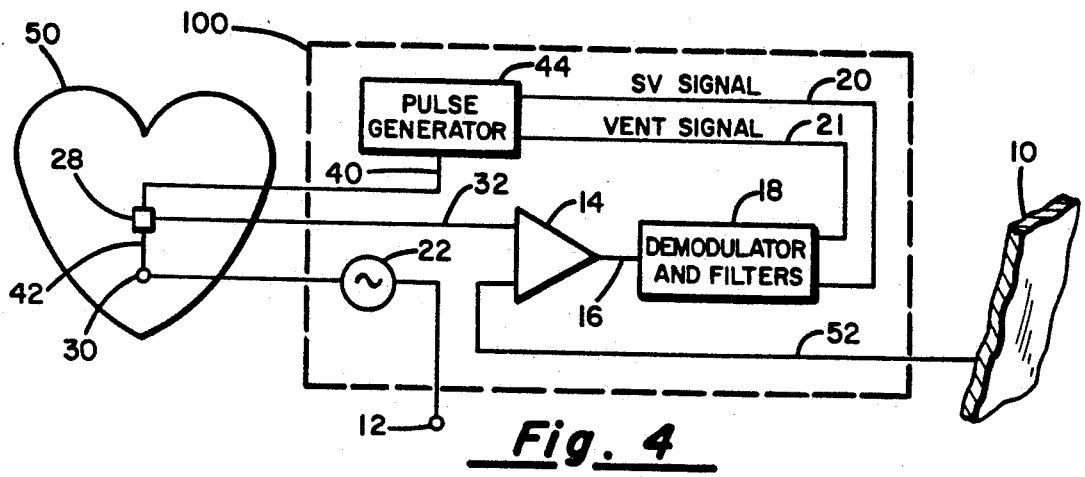
FIG. 4 schematically shows an alternative embodiment of a dual indifferent electrode apparatus differing from FIG. 2 in the manner in which the electrodes are driven and used for sensing.

FIG. 4 illustrates an alternative embodiment of the invention, again involving a bipolar lead 42 as in the embodiment of FIG. 2 but instead of connecting the oscillator 22 between the can 10 and the tip electrode 30, in the arrangement of FIG. 4, the oscillator 22 is connected between the tip electrode 30 and the button electrode 12 disposed on the insulating plastic top or header 11. Also, sensing takes place between the conductive metal can 10 and the ring electrode 28 On the endocardial lead 42. Specifically, the ring electrode 28 is connected by conductor 32 to a first input of the differential sense amplifier 14. A conductor 52 connects the can 10 to the second input of this differential sense amplifier. The oscillator 22 again produces an alternating current carrier signal at a frequency which is far higher than the patient's heart rate and, as indicated earlier, may fall into the range of from about 500 to 20000 Hz.

The signals fed into the sense amplifier 14 reflect impedance changes in the body tissue present between the location of the can 10 in the chest wall and the ring electrode 28 which would typically be in the right atrium of the heart. This modulation is removed by the demodulator and filters 18, again resulting in a ventilatory signal component on line 21 and a stroke volume related signal on line 20. These signals may be used individually or may be combined together in a predetermined algorithm with the resulting control signal used to adjust the rate at which pulse generator 44 emits pacing pulses to the tip electrode 30.

Figure 5:
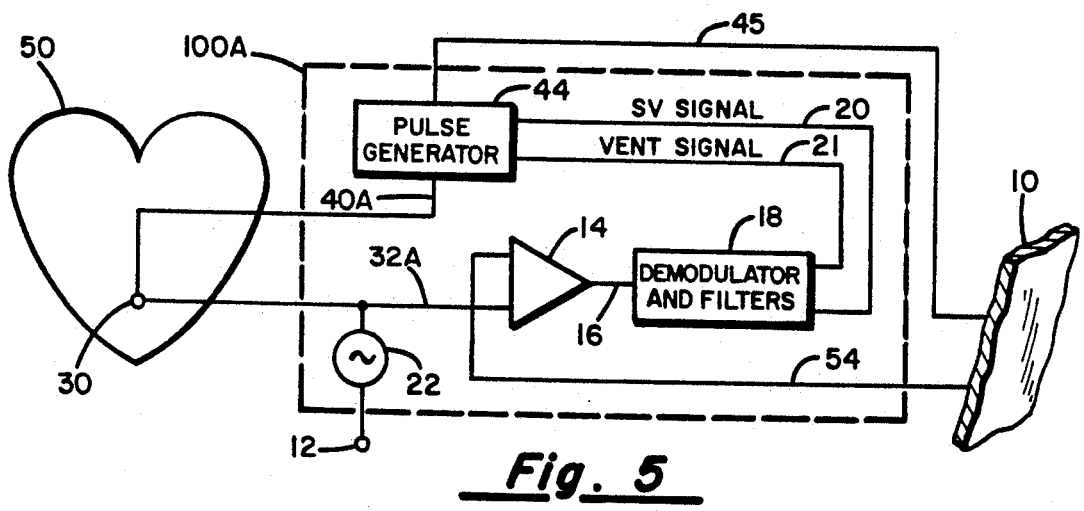
FIG. 5 schematically shows an alternate embodiment of a dual indifferent electrode apparatus employing a unipolar endocardial lead but differing from the embodiment of FIG. 3 in the manner the electrodes are configured.

FIG. 5 shows a further alternative embodiment of the invention related to FIG. 3 of the drawings in that it embodies a unipolar lead 40A. Rather than connecting the high frequency carrier signal oscillator 22 between the can 10 and the tip electrode 30, in the arrangement of FIG. 5, the carrier oscillator 22 is connected between the spot electrode 12 on the insulated header 11 of the pacemaker 2 and the tip electrode 30 of the lead. When configured in this way, sensing occurs between the can 10 and the tip electrode 30. That is to say, the first input to the differential amplifier 14 is connected by a conductor 54 to the metal can 10 housing the pacing circuitry while the conductor 32A joins the second input of the differential sense amplifier 14 to the tip electrode 30 of the monopolar pacing lead 40A.

The embodiments of FIGS. 4 and 5 thus provide alternative ways of configuring the drive and sense electrodes but in most respects, the operation of the pacer system is substantially the same as is directed in conjunction with the embodiments of FIGS. 2 and 3.

Figure 6:
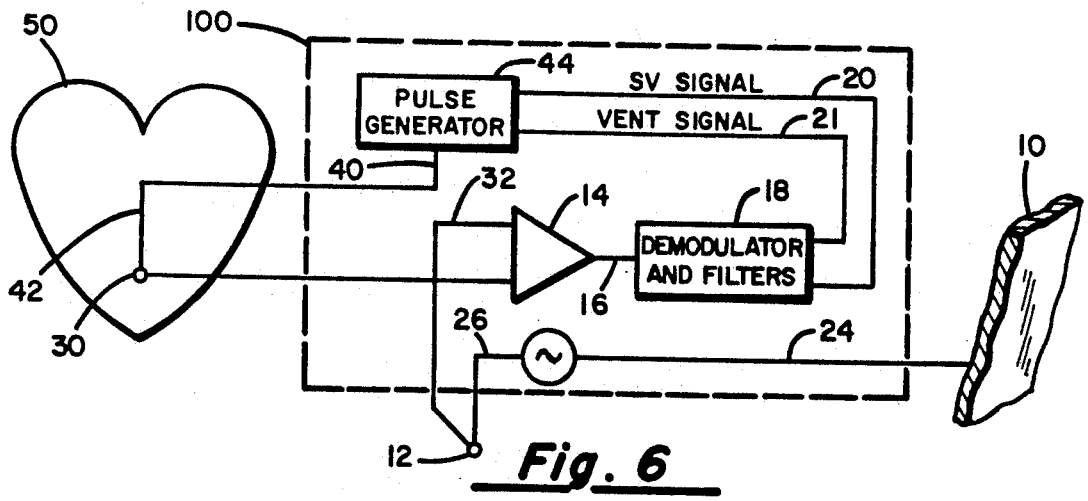
FIG. 6 schematically shows an alternate embodiment of a dual indifferent electrode apparatus for a pacer in which the drive voltage is applied between the pacer can and a spot electrode.

In the embodiment shown in FIG. 6, the oscillator 22 is coupled between the pacer can 10 and the button electrode 12. Sensing occurs between the monopolar tip electrode 30 on the pacing lead 42 and the button electrode 12. When a high frequency signal which may range between 500 Hz and 20000 Hz is applied between the can 10 and button electrode 12, the signal developed between electrode and tip electrode 30 and applied to the sense amplifier 14 is found to be modulated primarily by ventilatory activity rather than systolic activity. Thus, the output from the demodulator and filter circuit 18 on line 21 is signficiantly more dominating than the stroke volume signal present on line 20.

The invention has been described herein in considerable detail in order to comply with the patent statutes and to provide those skilled in the art with information needed to apply the novel principles and to construct and use such specialized components as are required. However, it is to be understood that the invention can be carried out by specifically different equipment and devices. For example, the control signal proportional to stroke volume change may be used in conjunction with an implantable infusion pump for administering such drugs as dobutamine, isoproterenol or nitroprusside whereby stroke volume may be maintained at a desired value. Alternatively, the demodulated waveform or control signal may be used directly by other diagnostic equipment. By appropriately utilizing the information derived from the ventricular impedance, it would be possible to measure stroke volume without having to resort to thermal dilution or other techniques. Hence, various modifications, both as to the equipment details and operating procedures can be effective without departing from the scope of the invention itself.

What is claimed is:

1. A variable rate cardiac pacer apparatus responsive to metabolic needs of a patient, wherein the cardiac pacer apparatus includes a pulse generator, comprising:
   (a) a source of alternating current carrier signals of a predetermined frequency;
   (b) an endocardial lead having at least first and second electrodes disposed thereon;
   (c) a pacer housing including a conductive pacer can;
   (d) a third electrode disposed on said housing and insulated from the pacer can;
   (e) sense amplifier means having first and second inputs and an output;
   (f) means coupling said source of alternating current carrier signals between said first electrode and one of said pacer can and said third electrode;
   (g) means coupling said first and second inputs of said sense amplifier means individually to the other of said pacer can and said third electrode and to said second electrode, respectively, for sensing at said output of said sense amplifier a modulated signal proportional to the instantaneous tissue impedance within the thoracic cavity;
   (h) demodulator and filter circuit means for demodulating said modulated signal and recovering a demodulated signal therefrom, said demodulated signal also being proportional to instantaneous impedance within the thoracic cavity wherefrom the demodulator and filter circuit means develops a control signal consistent with the instantaneous impedance in the thoracic cavity; and
   (i) means for applying said control signal to said pulse generator for modifying the pacing rate thereof.

2. The apparatus of claim 1 wherein the modulating signal includes a ventilatory signal component, and following demodulation, the ventilatory signal component is recovered, and said signal being proportional to instantaneous ventilation, is used to develop a heart rate control signal consistent with instantaneous or time-averaged ventilation.

3. The apparatus of claim 1 wherein the pacer apparatus includes an insulated top on said can and the third electrode resides exposed through the insulated top.

4. The apparatus of claim 1 wherein the predetermined carrier signal frequency is in a range from about 500 to 20000 Hz.

5. A variable rate cardiac pacer apparatus responsive to metabolic needs of a patient, wherein the cardiac pacer apparatus includes a pulse generator, comprising:
   (a) a source of alternating current carrier signals of a predetermined frequency;
   (b) a unipolar lead having a first electrode;
   (c) a pacer housing including a conductive pacer can;
   (d) a second electrode mounted on said pacer housing and insulated from the pacer can, in electrical contact with body tissue and structured and arranged to cooperate with the first electrode to form a pair of drive electrodes for said carrier signals;
   (e) sense amplifier means being coupled to said first electrode and said pacer can for receiving and amplifying a modulated carrier signal developed across said first electrode and said pacer can;
   (f) demodulator and filter circuit means for demodulating said modulated signal and recovering a demodulated signal therefrom, said demodulated signal being related to variations in thoracic impedance due to ventilatory activity wherefrom the demodulator and filter circuit means develops a control signal consistent with said ventilatory components; and
   (g) means for applying said control signal to the pulse generator to vary its pacing rate.

6. The apparatus of claim 5 wherein the pacer housing includes an insulated top and the second electrode resides exposed through the insulated top.

7. The apparatus of claim 5 wherein the predetermined carrier signal frequency is in the range of from about 500 to 20000 Hz.

8. A variable rate cardiac pacer apparatus responsive to metabolic needs of a patient, wherein the cardiac pacer apparatus includes a pulse generator, comprising:
   (a) a source of alternating current carrier signals of a predetermined frequency;
   (b) an endocardial lead having at least first and second electrodes disposed thereon;
   (c) a pacer housing including a conductive pacer can;
   (d) a third electrode disposed on said housing and insulated from the pacer can;
   (e) sense amplifier means having first and second inputs and an output;
   (f) means coupling said source of alternating current between only two of said pacer can, said first, said second and said third electrodes;
   (g) means coupling said first and second inputs of said sense amplifier means individually to other than the two of said pacer can, said first, second and third electrodes to which said source of alternating current is connected, for sensing at the output of said sense amplifier a modulating signal proportional to the instantaneous tissue impedance within the thoracic cavity;
   (h) demodulator and filter circuit means for demodulating said modulated signal and recovering a demodulated signal therefrom, said demodulated signal also being proportional to instantaneous impedance within the thoracic cavity wherefrom the demodulator and filter circuit means develops a control signal consistent with the instantaneous impedance in the thoracic cavity; and
   (i) means for applying said control signal to said pulse generator for modifying the pacing rate thereof.

9. A variable rate cardiac pacer apparatus responsive to metabolic needs of a patient, wherein the cardiac pacer apparatus includes a pulse generator, comprising:
   (a) a source of alternating current carrier signals of a predetermined frequency;
   (b) an endocardial lead having at least one electrode disposed thereon;
   (c) a pacer housing including a conductive pacer can;
   (d) a button electrode disposed on said housing and insulated from the pacer can;
   (e) sense amplifier means having first and second inputs and an output;
   (f) means coupling said source of alternating current carrier signals between said conductive pacer can and said button electrode;
   (g) means coupling said first and second inputs of said sense amplifier means individually to said one electrode and to said button electrode for sensing at the output of said sense amplifier a modulated signal proportional to the instantaneous tissue impedance within the thoracic cavity;
   (h) demodulator and filter circuit means for demodulating said modulated signal and recovering a demodulated signal therefrom, said demodulated signal also being proportional to instantaneous impedance within the thoracic cavity wherefrom the demodulator and filter circuit means develops control signal consistent with the instantaneous impedance in the thoracic cavity; and
   (i) means for applying said control signal to said pulse generator for modifying the pacing rate thereof.

* * * * *